United States Patent
Bardell et al.

(10) Patent No.: US 9,207,166 B2
(45) Date of Patent: Dec. 8, 2015

(54) MICRO-MOLDED CYTOMETER CARTRIDGE WITH INTEGRATED OPTICS

(71) Applicant: Honeywell International Inc., Morristown, NJ (US)

(72) Inventors: Ronald Bardell, St. Louis Park, MN (US); Jeffrey Shonkwiler, Hudson, WI (US)

(73) Assignee: Honeywell International Inc., Morris Plains, NJ (US)

( * ) Notice: Subject to any disclaimer, the term of this patent is extended or adjusted under 35 U.S.C. 154(b) by 145 days.

(21) Appl. No.: 13/755,536

(22) Filed: Jan. 31, 2013

(65) Prior Publication Data

US 2014/0211205 A1    Jul. 31, 2014

(51) Int. Cl.
  *G01N 1/10*   (2006.01)
  *G01N 21/05*  (2006.01)
  *G01N 15/14*  (2006.01)

(52) U.S. Cl.
  CPC ............ *G01N 21/05* (2013.01); *G01N 15/1484* (2013.01)

(58) Field of Classification Search
  CPC ......... G01N 21/05; G01N 1/10; G01N 21/00; B01L 3/00
  USPC ............. 356/246, 450–451, 436; 436/63, 173
  See application file for complete search history.

(56) References Cited

U.S. PATENT DOCUMENTS

| | | | |
|---|---|---|---|
| 6,382,228 B1 | 5/2002 | Cabuz | |
| 6,576,194 B1 | 6/2003 | Holl | |
| 6,597,438 B1 | 7/2003 | Cabuzc et al. | |
| 6,880,414 B2 | 4/2005 | Norton | |
| 7,336,812 B2 | 2/2008 | Dietz et al. | |
| 7,671,987 B2 | 3/2010 | Padmanabhan et al. | |
| 7,911,617 B2 * | 3/2011 | Padmanabhan et al. | 356/450 |
| 7,978,329 B2 | 7/2011 | Padmanabhan et al. | |
| 8,189,899 B2 | 5/2012 | Coumans et al. | |
| 8,273,294 B2 | 9/2012 | Padmanabhan et al. | |
| 2002/0149766 A1 * | 10/2002 | Bardell et al. | 356/246 |
| 2004/0025602 A1 | 2/2004 | Norton | |
| 2006/0023207 A1 * | 2/2006 | Cox et al. | 356/246 |
| 2007/0190525 A1 * | 8/2007 | Gu et al. | 435/5 |
| 2007/0269345 A1 | 11/2007 | Schilffarth et al. | |
| 2008/0195020 A1 * | 8/2008 | Cabuz et al. | 604/4.01 |
| 2012/0225475 A1 | 9/2012 | Wagner et al. | |
| 2012/0258488 A1 | 10/2012 | Abilez et al. | |

* cited by examiner

*Primary Examiner* — Tarifur Chowdhury
*Assistant Examiner* — Isiaka Akanbi
(74) *Attorney, Agent, or Firm* — Schwegman Lundberg & Woessner, P.A.

(57) ABSTRACT

A cytometer cartridge insert includes a micro-molded component and a plastic laminate component. The micro-molded component is embedded in the plastic laminate component.

17 Claims, 2 Drawing Sheets

MICRO-MOLDED CYTOMETER CARTRIDGE WITH INTEGRATED OPTICS

TECHNICAL FIELD

The present disclosure relates to cytometers, and in an embodiment, but not by way of limitation, a micro-molded cytometer cartridge with integrated optics.

BACKGROUND

Current cytometer cartridges have several limitations. Current cytometer cartridges require two orders of magnitude more sheath fluid than sample fluid. This volume of sheath fluid makes up most of the waste fluid and requires a relatively large cartridge size. Current cytometer cartridges require an optical system that resides on the cytometer instrument and that precisely aligns with the cytometer instrument and the illumination source and detectors of the instrument. Current cartridges further need to be able to search for, and lock onto, the stream of cells within the measurement channel. Current cartridges limit the range of scatter angles that can be detected to those angles that are much smaller than 30 degrees. Current cartridges require a precise sample via to inject sample into the reagent channel. Additionally, the dimensional tolerance of the sample via is one of the smallest on the cytometer cartridge card.

DETAILED DESCRIPTION

Figure 1:
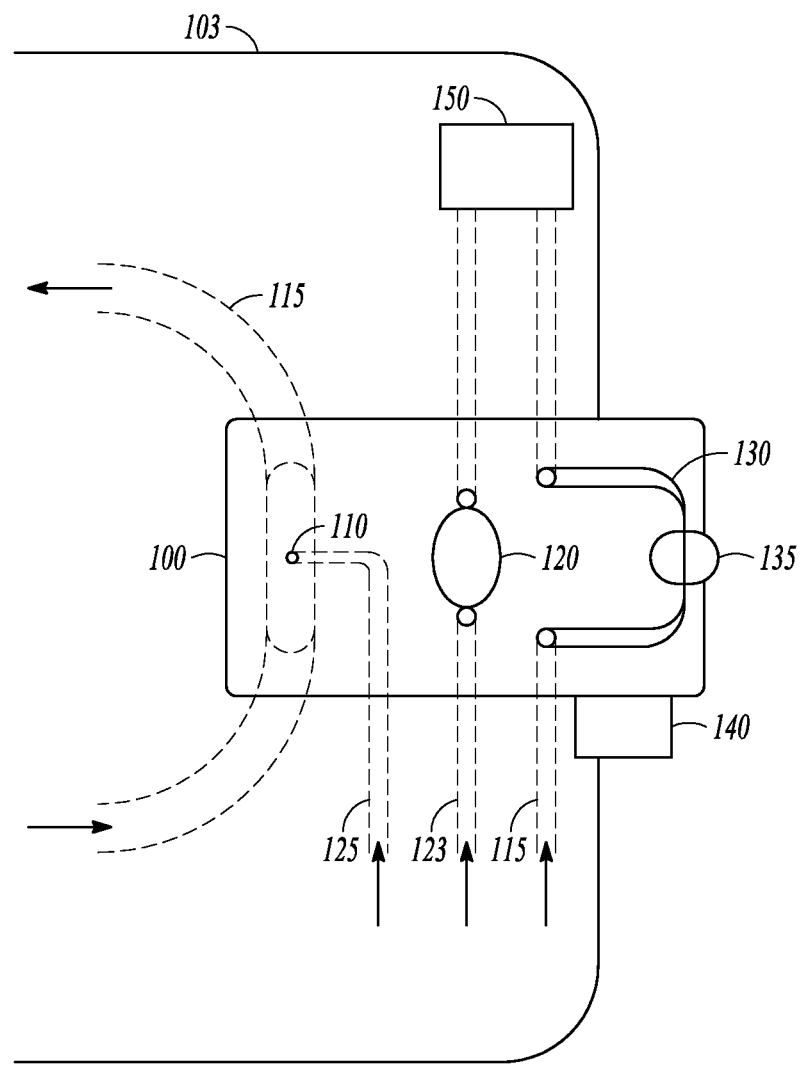
FIG. 1 illustrates an embodiment of a micro-molded cytometer cartridge with integrated optics.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, electrical, and optical changes may be made without departing from the scope of the present invention. The following description of example embodiments is, therefore, not to be taken in a limited sense, and the scope of the present invention is defined by the appended claims.

In a cytometer cartridge insert, a micro-molded component includes a measurement channel and one or more integrated optical lenses with alignment features. In an embodiment, the micro-molded component is embedded in a cytometer cartridge that is a plastic laminate cartridge. The alignment features ensure alignment between the integrated optical system on the cartridge and the light source and detectors on the instrument (i.e., via the manifold of the cytometer instrument). The micro-molding process ensures that the measurement channel walls of the integrated optical system have a low RMS planarity level and good optical finish characteristics. The light scatter from the illumination beam on the walls has the same group of angles as the beam and thus occupies only a small solid angle of the total budget of angles and will not produce random scatter noise. This allows a cell stream to be close to the measurement channel walls, which reduces the need for a sheathing fluid, as the lysing and sphering fluids will provide sufficient sheathing of the cell stream. Elimination of the sheathing fluid requirement dramatically reduces the amount of liquid waste and the size of the on-cartridge waste chamber.

The integrated optical lenses also allow detection of scatter angles as large as 90 degrees. As is known in the art, a larger scatter angle provides more information about the cells and easier differentiation among cell types. The micro-molded component also includes other small tolerance features of the cartridge insert, such as a hemoglobin measuring cuvette and a sample via. The micro-molded component can be produced with a lower manufacturing cost of the plastic laminate cartridge. The relatively small footprint of the micro-molded component in relation to its thickness allows manufacture of the component using injection molding. In contrast, the use of injection molding for a full card layer would result in a relatively inefficient fabrication process.

A micro-molded insert for the proposed cytometer cartridge includes a measurement channel (e.g., having a diameter ranging from 20 microns to 200 microns) with integrated optical lenses, a sample via, and a hemoglobin measuring cuvette. The molded component is integrated into a plastic laminate cartridge containing a sample tank, a lysing/sphering channel, a hemoglobin reagent channel, and waste chamber. Fixed laser and optical detectors are mounted in a rigid manifold in the cytometer instrument. When the cartridge is loaded into the instrument, registration surfaces on the micro-molded insert contact similar registration surfaces on the laser and detector assembly of the cytometer instrument for precise positioning.

As noted above, sheathing fluid need not be used in connection with the cytometer cartridge insert. The sample via causes the lysing and sphering solutions to sheath the sample fluid sufficiently so that the blood cells are focused to flow near the center of the channel. The integrated optical system and the small diameter of the measurement channel ensure that all cells are interrogated by the laser. Consequently, a typical cytometer protocol applies, except that there is no sheathing fluid to start up prior to counting cells, so there are no sheath fluid bubbles to clear, and since the laser and detectors are registered to the micro-molded insert in the cartridge, there is no laser alignment step.

Additionally, since optical lenses are implemented as part of the measurement channel, they can be precisely oriented for scatter detection at optimal angles, for example, within 2-9 degrees, within 9-20 degrees, and at 90 degrees. The hemoglobin measuring cuvette, which has a tight tolerance on its optical path length dimension, and the sample via, which has a tight tolerance on its diameter and position, are both implemented in the micro-molded insert.

FIG. 1 illustrates an example embodiment of a micro-molded cytometer cartridge with integrated optics. The cartridge includes a micro-molded component 100 and a plastic laminate component 103. The micro-molded component 100 is embedded in the plastic laminate component 103.

As further illustrated in FIG. 1, the micro-molded component 100 includes several features. The sample via 110 transmits blood sample from channel 125 to channel 115. In an embodiment, the sample via 110 has a diameter ranging from approximately 30 microns to approximately 100 microns. The ability to manufacture a sample via of this size is possible by using micro-molding techniques. The micro-molded component 100 further includes a measurement channel 130 with integrated optical lenses 135. The measurement channel 130 is coupled to the sample via 110 by way of a lysing and sphering channel 115. The measurement channel 130 has a diameter ranging from approximately 20 microns to approximately 200 microns. The length of the measurement channel 130 can range from about 100 microns to 2500 microns. The diameter of the sample via 110 and the measurement channel 130 permits the use of no sheathing fluid, and the diameter further results in a single stream of cells. The micro-molded component 100 also includes a cuvette 120. In an embodiment, the cuvette is a hemoglobin measuring cuvette. Blood or other sample is supplied to the cuvette 120 by way of a channel 123. The channel 123 is also coupled to the same source of sample as channel 125. Both the sample via 110 and the cuvette 120 contain the same sample. The cuvette 120 can range in diameter from about 250 microns to about 3500 microns. In an embodiment, the cuvette 120 has an optical mask around it on the light detector side so as to block any light scatter.

The cytometer cartridge includes an alignment device 140 for aligning the integrated optical lens with a light source and a light detector. The light source and the light detector are normally located on the cytometer instrument. In an embodiment, the alignment device is a three-point registration surface, which is configured or manufactured to couple with a mating registration surface of a manifold of the cytometer instrument. Additionally, the integrated optical lens 135 is aligned with the measurement channel such that the light scatter from the illumination beam on the optically-smooth measurement channel walls occupies only a small solid angle of the total budget of angles and will not produce random scatter noise.

The plastic laminate component 103 includes a waste chamber 150. The waste chamber 150 is coupled to the cuvette 120 and the measurement channel 130, such that it serves as a receptacle for the sample after it has been analyzed in the cuvette or measurement channel. The micro-molding manufacture of the cartridge 100 permits a very small scale manufacture of the sample via 110, measurement channel 130, cuvette 120, and other related components. In an embodiment, the waste chamber has a volume of approximately 3 milliliters. The plastic laminate component 103 further includes a lysing and sphering channel, a reagent channel, and a sample tank.

Figure 2:
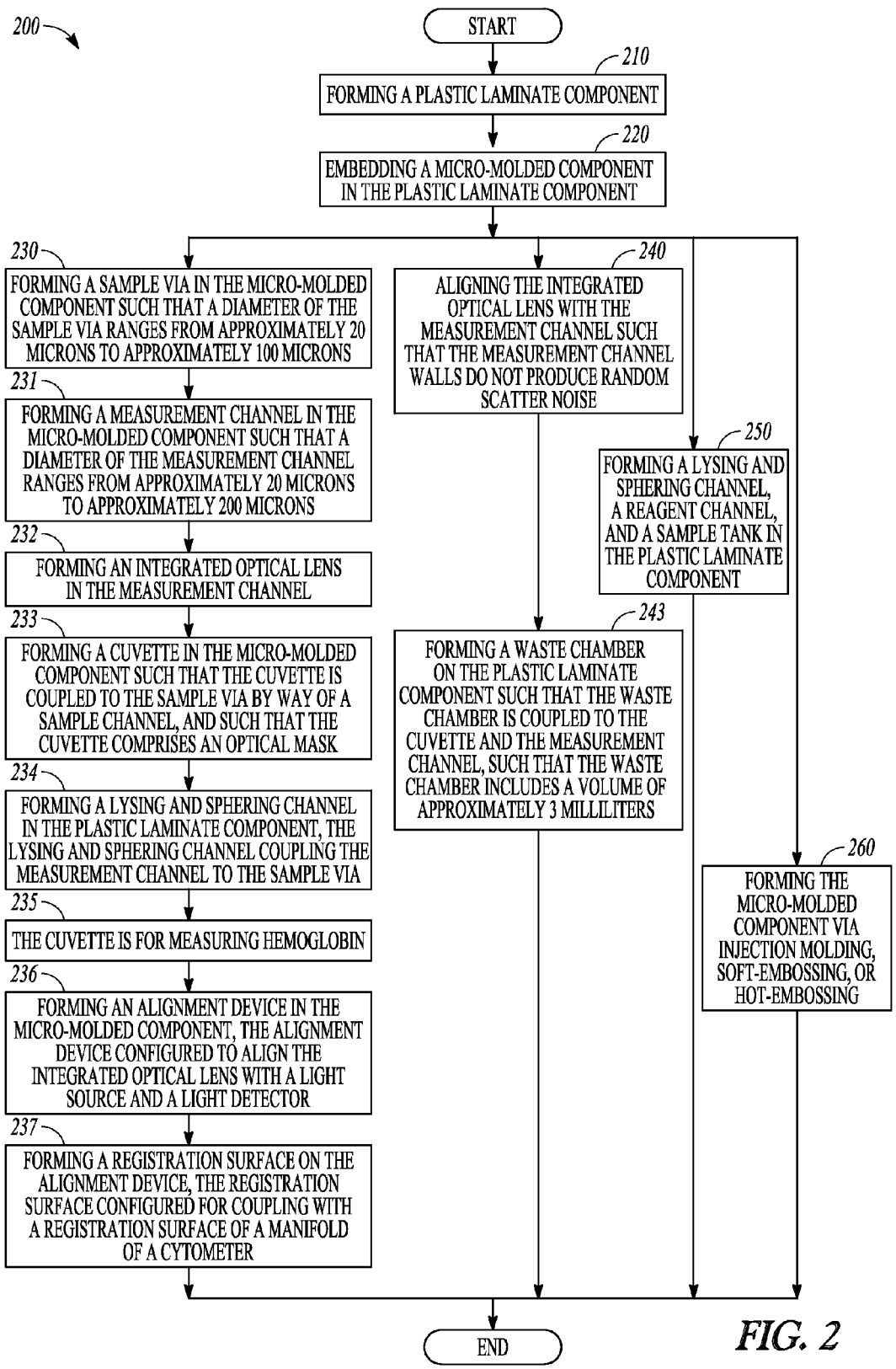
FIG. 2 is a flowchart of an example embodiment to manufacture a cytometer cartridge with integrated optics.

FIG. 2 is a flowchart of an example embodiment of a process 200 to manufacture a cytometer cartridge with integrated optics. FIG. 2 includes a number of process and feature blocks 205-260. Though arranged substantially serially in the example of FIG. 2, other examples may reorder the blocks, omit one or more blocks, and/or execute two or more blocks in parallel using multiple processors or a single processor organized as two or more virtual machines or sub-processors. Moreover, still other examples can implement the blocks as one or more specific interconnected hardware or integrated circuit modules with related control and data signals communicated between and through the modules. Thus, any process flow is applicable to software, firmware, hardware, and hybrid implementations.

Referring now to FIG. 2, at 210, a cytometer cartridge insert is manufactured by forming a plastic laminate component, and at 220, embedding a micro-molded component in the plastic laminate component.

At 230, a sample via is formed in the micro-molded component such that the diameter of the sample via ranges from approximately 20 microns to approximately 100 microns. At 231, a measurement channel is formed in the micro-molded component such that a diameter of the measurement channel ranges from approximately 20 microns to approximately 200 microns. At 232, an integrated optical lens is formed in the measurement channel. At 233, a cuvette is formed in the micro-molded component. As noted above, the cuvette is coupled to a sample channel that is also coupled to the sample via. As noted in block 235, the cuvette can be for measuring hemoglobin. At 234, a lysing and sphering channel is formed in the plastic laminate component. The lysing and sphering channel couple the measurement channel to the sample via.

At 236, an alignment device is formed in the micro-molded component. The alignment device is manufactured or configured to align the integrated optical lens with a light source and a light detector. At 237, a registration surface is formed on the alignment device. The registration surface is manufactured or configured for coupling with a registration surface of a manifold of a cytometer instrument. At 240, the integrated optical lens is aligned with the measurement channel such that the measurement channel walls do not produce random scatter noise. As noted above, this alignment of the optical lens and measurement channel insures that light scatter from the illumination beam on the optically-smooth measurement channel walls occupies only a small solid angle of the total budget of angles and will not produce random scatter noise.

At 243, a waste chamber is formed on the plastic laminate component such that the waste chamber is coupled to the cuvette and the measurement channel. As noted above, in a typical embodiment, the waste chamber has a volume of approximately 3 milliliters. This small volume is made possible by the reduced size of the micro-molded components compared to prior art cytometers. At 250, a lysing and sphering channel, a reagent channel, and a sample tank are formed in the plastic laminate component. At 260, the micro-molded component is formed by injection molding, soft-embossing, or hot-embossing.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. An apparatus comprising:
   a cytometer cartridge insert, the cytometer cartridge insert comprising:
      a micro-molded component; and
      a plastic laminate component;
   wherein the micro-molded component is embedded in the plastic laminate component;
   wherein the micro-molded component comprises:
      a sample via comprising a diameter ranging from approximately 20 microns to approximately 100 microns;
      a measurement channel with an integrated optical lens, the measurement channel coupled to the sample via by way of a lysing and sphering channel, the measurement channel comprising a diameter ranging from approximately 20 microns to approximately 200 microns, the integrated optical lens permitting detection of scatter angles of about 90 degrees; and
      a cuvette coupled to the sample via by way of a sample channel, the cuvette comprising an optical mask;
   wherein the integrated optical lens is aligned with the measurement channel such that the measurement channel walls do not produce random scatter noise; and wherein the measurement channel walls have a low RMS planarity level and optical finish characteristics such that an illumination beam on the walls generates light scatter having a same group of angles as the illumination beam, thereby occupying a small solid angle of a budget of angles and not producing the random scatter noise, thereby providing for a cell stream to be close to the measurement channel walls, thereby reducing the need for a sheathing fluid and reducing an amount of liquid waste.

2. The cytometer cartridge insert of claim 1, wherein the cuvette comprises a cuvette for measuring hemoglobin.

3. The cytometer cartridge insert of claim 1, comprising an alignment device for aligning the integrated optical lens with a light source and a light detector on a cytometer instrument.

4. The cytometer cartridge insert of claim 3, wherein the alignment device comprises a three point registration surface configured to couple with a registration surface of a manifold of a cytometer.

5. The cytometer cartridge insert of claim 1, wherein the plastic laminate component comprises a waste chamber coupled to the cuvette and the measurement channel, the waste chamber comprising a volume of approximately 3 milliliters.

6. The cytometer cartridge insert of claim 1, wherein the plastic laminate component comprises a lysing and sphering channel, a reagent channel, and a sample tank.

7. The cytometer cartridge of claim 1, wherein the micro-molded component comprises an injection molded component, a soft-embossed component, or a hot-embossed component.

8. A process to manufacture a cytometer cartridge insert comprising:
    forming a plastic laminate component; and
    embedding a micro-molded component in the plastic laminate component;
    forming a sample via in the micro-molded component such that a diameter of the sample via ranges from approximately 20 microns to approximately 100;
    forming a measurement channel in the micro-molded component by way of a micro-molded process such that a diameter of the measurement channel ranges from approximately 20 microns to approximately 200 microns and such that a wall of the measurement channel has a low RMS planarity level and optical finish characteristics such that an illumination beam on the wall generates light scatter having a same group of angles as the illumination beam, thereby occupying a small solid angle of a budget of angles and producing no random scatter noise;
    forming an integrated optical lens in the measurement channel, the integrated optical lens oriented for scatter detection of angles between 2-9 degrees, between 9-20 degrees, and at 90 degrees;
    forming a cuvette in the micro-molded component such that the cuvette is coupled to the sample via by way of a sample channel, and such that the cuvette comprises an optical mask;
    forming a lysing and sphering channel in the plastic laminate component, the lysing and sphering channel coupling the measurement channel to the sample via.

9. The process to manufacture a cytometer cartridge insert of claim 8, wherein the cuvette comprises a hemoglobin cuvette.

10. The process to manufacture a cytometer cartridge insert of claim 8, comprising forming an alignment device in the micro-molded component, the alignment device configured to align the integrated optical lens with a light source and a light detector.

11. The process to manufacture a cytometer cartridge insert of claim 10, comprising forming a three point registration surface on the alignment device, the registration surface configured for coupling with a registration surface of a manifold of a cytometer.

12. The process to manufacture a cytometer cartridge insert of claim 8, comprising aligning the integrated optical lens with the measurement channel such that the measurement channel walls do not produce random scatter noise; and forming the measurement channel walls having a low RMS planarity level and optical finish characteristics such that an illumination beam on the walls generates light scatter having a same group of angles as the illumination beam, thereby occupying a small solid angle of a budget of angles and not producing the random scatter noise.

13. The process to manufacture a cytometer cartridge insert of claim 8, comprising forming a waste chamber on the plastic laminate component such that the waste chamber is coupled to the cuvette and the measurement channel, and such that the waste chamber comprises a volume of approximately 3 milliliters.

14. The process to manufacture a cytometer cartridge insert of claim 8, comprising forming a lysing and sphering channel, a reagent channel, and a sample tank in the plastic laminate component.

15. The process to manufacture a cytometer cartridge insert of claim 8, comprising forming the micro-molded component via injection molding, soft-embossing, or hot-embossing.

16. A cytometer cartridge insert comprising:
    a micro-molded component; and
    a plastic laminate component;
wherein the micro-molded component is embedded in the plastic laminate component; and
wherein the micro-molded component comprises:
    a sample via comprising a diameter ranging from approximately 20 microns to approximately 100;
    a measurement channel with an integrated optical lens, the measurement channel coupled to the sample via by way of a lysing and sphering channel, the measurement channel comprising a diameter ranging from approximately 20 microns to approximately 200 microns; and
    a cuvette coupled to the sample via by way of a sample channel, the cuvette comprising an optical mask;
    wherein the integrated optical lens is aligned with the measurement channel such that the measurement channel walls do not produce random scatter noise; and wherein the measurement channel walls have a low RMS planarity level and optical finish characteristics such that an illumination beam on the walls generates light scatter having a same group of angles as the illumination beam, thereby occupying a small solid angle of a budget of angles and not producing the random scatter noise.

17. The cytometer cartridge insert of claim 16, comprising an alignment device for aligning the integrated optical lens with a light source and a light detector; wherein the alignment device comprises a registration surface configured to couple with a registration surface of a manifold of a cytometer.

* * * * *